(12) United States Patent
Dougherty et al.

(10) Patent No.: US 6,613,569 B1
(45) Date of Patent: Sep. 2, 2003

(54) INDUCIBLE PACKAGING CELL LINES FOR LENTIVIRUS VECTORS

(75) Inventors: Joseph P Dougherty, Hampton, NJ (US); Martin E Adelson, Hillsborough, NJ (US); Malvika Kaul, Piscataway, NJ (US); AnnMarie L Pacchia, Piscataway, NJ (US); Yacov Ron, East Brunswick, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/979,681

(22) PCT Filed: May 25, 2000

(86) PCT No.: PCT/US00/14448
§ 371 (c)(1),
(2), (4) Date: Mar. 5, 2002

(87) PCT Pub. No.: WO00/71678
PCT Pub. Date: Nov. 30, 2000

Related U.S. Application Data

(60) Provisional application No. 60/135,949, filed on May 25, 1999.

(51) Int. Cl.[7] .............................. C12N 5/08; C12N 5/10; C12N 13/86
(52) U.S. Cl. ..................... 435/457; 435/69.1; 435/69.3; 435/235.1; 435/236; 435/320.1; 435/366; 435/369; 435/325; 435/440; 435/458; 435/456; 435/377; 435/367; 514/44; 536/23.72
(58) Field of Search .............................. 435/69.1, 69.3, 435/369, 325, 366, 440, 455, 456, 457, 458, 236, 320.1, 91.4; 514/44; 536/23.72

(56) References Cited

U.S. PATENT DOCUMENTS 6,218,181 B1 * 4/2001 Verma et al. ............... 435/369

OTHER PUBLICATIONS

Malvika Kaul et al, Regulated Lentiviral Packaging Cell Line Devoid of Most Viral cis–Acting Sequences, virology 249, 167–174 1998.*

David No et al, Ecdysone–inducible gene expression in mammalian cells and transgenic mice, vol. 93, pp. 3346–3351, Apr. 1996.*

Christopherson et al., "Ecdysteroid–dependent regulation of genes in mammalian cells by a *Drosophila* ecdysone receptor and chimeric transactivators," Proc. Natl. Acad. Sci. USA, vol. 89, (Jul. 1992) pp. 6314–6318.

Gingrich et al., "Inducible Gene Expression In the Nervous System of Transgenic Mice," Annu. Rev. Neurosci. (1998) pp. 377–405.

Kafri et al., "A Packaging Cell Line for Lentivirus Vectors," J. Virology, vol. 73, No. 1, (Jan. 1999) pp. 567–584.

Sawicki et al., "Cell–Specific Ecdysone–Inducible Expression of FLP Recombinase in Mammalian Cells," BioTechniques, vol. 25, (Nov. 1998) pp. 868–875.

Yu et al., "Inducible Human Immunodeficiency Virus Type 1 Packaging Cell Lines," J. Virology, vol. 70, No. 7, (Jul. 1996), pp. 4530–4537.

* cited by examiner

*Primary Examiner*—David Guzo
*Assistant Examiner*—Maria Marvich
(74) *Attorney, Agent, or Firm*—Perkins Coie LLP

(57) ABSTRACT

Novel packaging cell lines for production of lentiviral vectors are disclosed. The cell lines utilize an ecdysone-inducible system for virus production, thereby avoiding the cytotoxic effect of unregulated expression of certain envelope proteins and lentiviral proteins. Various embodiments of the cell lines are disclosed, which are suitable for different purposes that range from in vitro screening assays to gene therapy in vivo.

5 Claims, 6 Drawing Sheets

INDUCIBLE PACKAGING CELL LINES FOR LENTIVIRUS VECTORS

This application claims priority to U.S. Provisional Application No. 60/135,949, filed May 25, 1999, the entirety of which is incorporated by reference herein.

Pursuant to 35 U.S.C. §202(c), it is acknowledged that the United States Government has certain rights in the invention described herein, which was made in part with funds from the National Institutes of Health, Grant Nos.CA50777, NS38272, AI43886 and AI34834.

FIELD OF THE INVENTION

The present invention relates generally to the fields of molecular biology and genetic engineering. More specifically, the invention provides inducible packaging cell lines for production of lentivirus vectors.

BACKGROUND OF THE INVENTION

Various publications or patents may be referenced in this application to describe the state of the art to which the invention pertains. Each of these publications or patents, is incorporated by reference herein.

Retroviral vectors and packaging cells are important tools for gene transfer into eucaryotic cells. Replication-defective retroviral vectors contain the cis-acting sequences required for efficient virus replication. The packaging cell lines provide viral proteins required in trans for virus replication. Introduction of a retroviral vector into a suitable packaging cell enables the propagation of vector virus in the absence of replication-competent virus.

Most retroviral vectors have been derived from oncoviruses, such as murine leukemia virus (MLV). A limitation of oncovirus-based systems is that proviral integration into the host genome requires at least one round of cell division.

In contrast, the preintegration complex of the lentivirus, human immunodeficiency virus-1 (HIV-1), can integrate into the genomes of non-dividing cells. This feature, among others, of HIV-1 has provided incentive for the development of HIV-1 packaging cell systems for use in in vivo gene therapy. In addition, HIV-1 packaging cell lines can be used to study HIV-1 replication, mutation frequencies and latency.

The HIV-1 genome codes for the proteins Gag, Pol, and Env which are common to all retroviruses. In addition, it contains two regulatory genes, tat and rev, which are important for efficient viral replication, and four accessory genes, vif, vpr, spit, and nef, which have been demonstrated to, be dispensable for HIV-1 vector production from transfected cells.

Several biological features of HIV-1 are obstacles to the development of safe, efficient HIV-1 based packaging lines. For instance, the pathogenicity associated with the virus requires that viral stocks be completely void of replication-competent virus. Also, as mentioned, HIV-1 expresses several accessory proteins reported to enhance high-level infection and replication. In some instances (e.g., for drug screening systems), it would be desirable to include them in packaging cell lines. However, several of the trans-acting proteins, including Env, have been reported to be cytotoxic or cytostatic, hampering the establishment of a constitutively expressing packaging cell line.

One way to circumvent the cytotoxicity of constitutively-expressed HIV-1 accessory proteins is to develop a system for inducibly expressing the proteins. Furthermore, inducible packaging cells provide a safe system for drug screening, since viral proteins are not produced until induction, and biologically hazardous wild-type virus is never generated.

Inducible HIV-1 packaging cell lines have been developed. For instance, Yu et al. (J. Virol. 70: 4530–4537, 1996) reported an HIV-1 packaging cell line that utilized the tetracycline-inducible expression system to control the expression of the Rev regulatory protein, which in turn controls expression of late proteins, including Gag, Pol and Env. Kaul et al. (Virology 249: 167–174, 1998) reported a tetracycline-inducible HIV-1 packaging cell line which, unlike its predecessor (Ku et al, 1996, supra), was capable of expressing all HIV-1 structural, regulatory and enzymatic proteins, but lacked a majority of the cis-acting sequences. Kafri et al. (J. Virol. 73: 576–584, 1999) reported the development of a VSV-G pseudotyped, tetracycline-inducible HIV-1 packaging cell line, which further expressed the Green Fluorescent Protein (GFP). The use of VSV-G bolsters virus titers, but concomitantly results in loss of target cell specificity.

The tetracycline-inducible system is effective, but has limitations. For instance, establishing appropriate expression levels for the DNA constructs used in the system can be difficult, due to the toxicity associated with the transactivation protein utilized in the induction system. This protein must be expressed in sufficient quantity to effect adequate induction of the HIV-1 proteins, but production of too much of the protein is toxic to the cells.

Thus, improvements in lentivirus packaging cell lines are needed and would advance the art of lentivirus based gene therapy and assay systems. Such improvements include inducible systems that are easy to establish and use, and that produce higher vector titers that those obtainable with current systems.

SUMMARY OF THE INVENTION

According to one aspect of the present invention, a transgenic mammalian packaging cell line for producing lentiviral vectors is provided. The cell line comprises (a) a DNA construct expressing a transcription factor responsive to ecdysone or an analog of ecdysone; and (b) one or more DNA constructs comprising one or more selected lentivirus genes required for packaging of a lentiviral vector; and a gene encoding a viral envelope protein. The lentivirus genes and the gene encoding the viral envelope protein are operably linked to at least one DNA response element acted upon by the transcription factor, and the cell line is transfectable with the lentiviral vector. The cell line preferably produces HIV-1 based vectors, and preferably is generated from 293T cells.

In one embodiment, the cell line includes a gene encoding an HIV-1 envelope protein. In another embodiment, the cell line includes a gene encoding a VSV-G envelope protein. In certain embodiments of the HIV-1 based cell line, the line expresses HIV-1 core genes, accessory genes and regulatory genes. In particularly preferred embodiments, the HIV-1 core and accessory genes and the HIV-1 env gene are introduced into the cell line on separate vectors. In other embodiments, the cell line is deleted for at least one HIV-1 accessory gene or regulatory genes, and preferably is deleted for all HIV-1 accessory genes except rev.

According to another aspect of the invention, a method for producing a lentivirus vector stock is provided. The method utilizes the above-described packaging cell line and comprises transfecting the cell line with the lentivirus vector and exposing the transfected cell line to ecdysone or an analog of ecdysone (preferably ponasterone A), for a time and under conditions enabling activation of the transcription factor and resultant induction of expression of the genes operably linked to the DNA response element. Thus, the proteins required for packaging of the lentiviral vector into virus particles are generated, resulting in production of the lentivirus vector stock.

Other features and advantages of the present invention will be better understood by reference to the drawings, detailed descriptions and examples that follow.

BRIEF DESCRIPTION OF THE DRAWINGS

FIG. 6. Expression of viral proteins.

DETAILED DESCRIPTION OF THE INVENTION

I. Definitions

Figure 1:
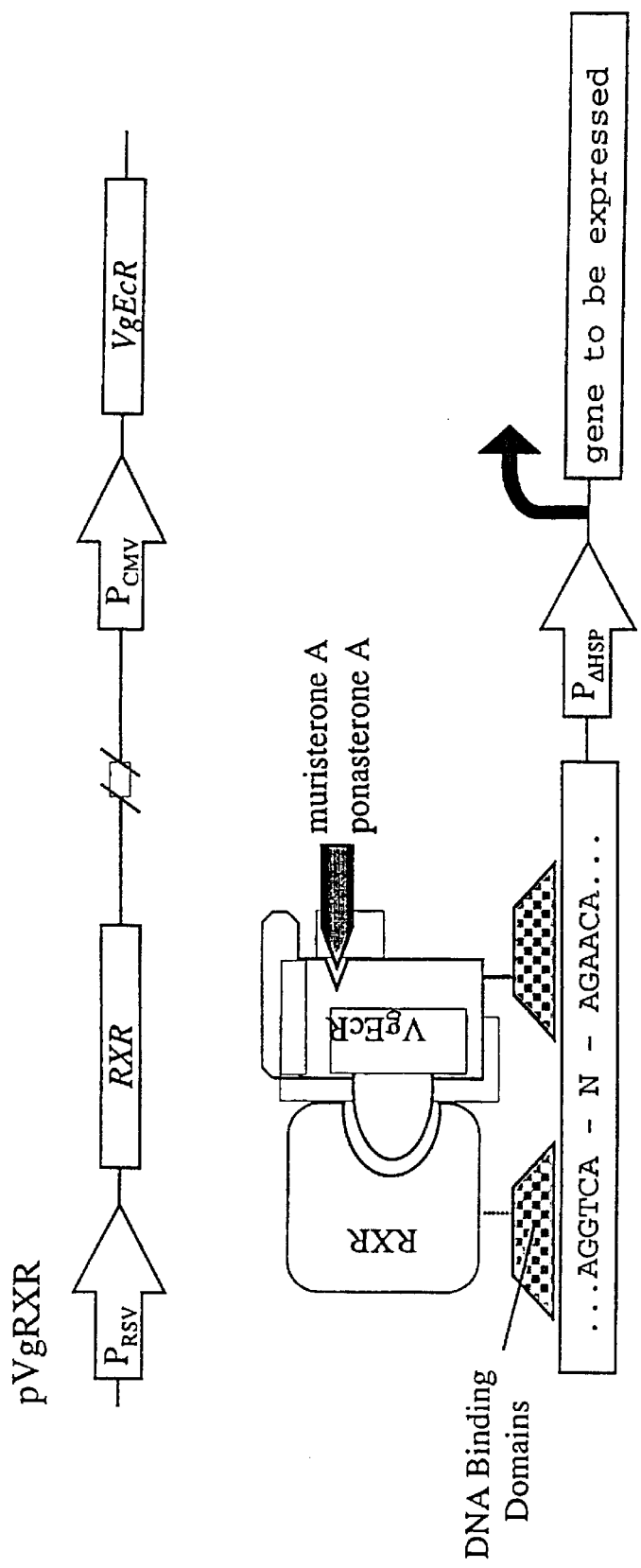
FIG. 1. Schematic diagram of the ecdysone inducible system.

Various terms relating to the present invention are used hereinabove and also throughout the specifications and claims.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "transcription factor" is a protein or protein complex that induces (or de-represses) transcription of a gene by recognizing and interacting with a cognate regulatory sequence of the gene, referred to herein as a "transcription factor response element". The transcription factor response element can be operably linked to various coding sequences, thereby imparting inducible expression to those coding sequences, upon interaction with the cognate transcription factor. Generally, and for purposes herein, transcription factors are themselves activate by contact with specific ligands. In the instant case, the transcription factor is activated by exposure to ecdysone or an analog of ecdysone. Accordingly, the term "ecdysone transcriptional control" and similar terms refer to the control of expression of a coding sequence by an ecdysone (or analog)-responsive transcription factor that induces transcription of the coding sequence operably linked to the cognate "ecdysone response" DNA element.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A cell has been "transformed" or "transfected" by exogenous or heterologous DNA when such DNA has been introduced inside the cell. The transforming DNA (transgene) may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations. If germline cells are stably transformed, the transformation may be passed from one generation of animals arising from the germline cells, to the next generation. In this instance, the transgene is referred to as being inheritable.

When lentivirus or HIV proteins or genes are referred to herein, the following usage is intended: core proteins or genes are Gag, Pol and Env, regulatory proteins or genes are Tat and Rev, accessory proteins or genes are Vif, Vpr, Vpu and Nef. However, the regulatory proteins/genes are sometimes referred to collectively as accessory proteins/genes, according to art-recognized usage.

Other definitions are found in the description set forth below.

II. Description

The present invention provides novel inducible lentivirus packaging cell lines possessing features superior to those of currently available inducible systems. The cell lines differ in the presence or absence of accessory proteins and the tropism afforded by the envelope protein. The cell lines have a common feature in that they all express HIV-1 proteins under tight regulation of an inducible promoter from Drosophila melanogaster. Transcription from this promoter element is upregulated only in the presence of the steroid hormone ecdysone, or one of its analogs. In accordance with the present invention, this regulated expression system has been demonstrated to overcome the cytotoxic and cytostatic effects resulting from the constitutive expression of certain HIV-1, proteins.

One exemplary cell line of the invention is a lineage-specific (i.e., producing the native HIV-1 Env protein) line that produces all HIV-1 proteins. This packaging cell line was generated by the stable, successive transfection and selection of four vectors into 293T cells. The first two vectors, pVgRXR and HIV-1gp, contain the ecdysone transcriptional factor-encoding gene and the HIV-1 gag, pol and accessory genes, respectively. The third vector produces the authentic HIV-1 envelope protein under ecdysone transcriptional control, which permits selective infection of CD4+ expressing human cells. The final vector contains the HIV-1 sequence which is packaged into the viral particle and can stably transfer expression of Green Fluorescent Protein (GFP) and puromycin resistance to infected cells. To increase biosafety, a majority of the HIV-1 cis-acting sequences considered important for HIV-1 genome encapsidation, including all of the 5'LTR and part of the 3'LTR, were removed. Moreover, the gag-pol and env genes were separated by splitting expression from two different plasmids. This vastly increases the likelihood that the viral genes will integrate at different locations in the host genome, thereby decreasing the probability of recombination to form wild-type virus. Such a safety feature is critical for use of the cell lines for gene therapy. However, for other purposes (e.g., drug screening), cell lines that express gag, pol and env from a single plasmid may also be utilized.

This packaging cell line produces vector titers approximately one log higher than currently available inducible cell lines produced in conjunction with the HIV-1 envelope. This cell line is described in greater detail in Example 1.

Another exemplary cell line of the present invention produces HIV-1 core proteins with a VSV-G envelope protein. This packaging cell line was generated as described above for the HIV-1env packaging cell line, but produces a different envelope protein, which is encoded by a pEc-VSV-G vector. Upon induction with ponasterone A, the vesicular stomatitis virus G protein (VSV-G) is produced instead of the HIV-1 envelope protein. These cell lines form pseudotyoed vector virus with VSV-G, which have the advantage of having a broad host range. These viral vectors can be concentrated by simple centrifugation, without significant loss of viral infectivity. It has been reported that such vectors can be concentrated more than a thousand-fold (Kafri et al., 1999, Supra), making in vivo application more tractable.

Another exemplary packaging cell line of the invention is deleted for production of most or all of the HIV-1 accessory proteins, and produces a VSV-G envelope protein. A preferred cell line of this type is deleted of all accessory proteins but Rev. This packaging cell line was generated with deletions of most or all HIV-1 accessory proteins to increase the biosafety levels of the inducible lentiviral packaging cell line. It has been demonstrated by triple transient transfection procedures that the accessory proteins are not required for efficient infection of target cells. The cell line is pseudotyped with the VSV-G protein, permitting an expanded host range and the ability to concentrate virus particles by centrifugation. For clinical trials, the absence of HIV-1 accessory proteins prevents formation of wild-type virus through recombination, and also reduces the likelihood of additional cytotoxic and immunological responses stemming from the transfer vectors.

A exemplary packaging cell line of this type is described in detail in Example 2; This vector is a safe, stable packaging cell line that is devoid of HIV-1 tat, vif, vpr, vpu and nef. Using this cell line, the inventors have been able to consistently generate concentrated pseudotyped vector virus stocks with titers in the range of $10^8$ IU/ml, which can efficiently transduce actively dividing and growth arrested cells in vitro.

It will be appreciated by persons skilled in the art that the features of the three aforementioned cell lines may be interchanged. For instance, an HIV env expressing system may be used in conjunction with a system depleted of accessory proteins. Furthermore, other envelope proteins may be used instead of VSV-G to alter or expand the host cell range of viral vectors produced by the packaging system. Any envelope protein may be suitable for this purpose. Examples of particularly suitable envelope proteins include, but are not limited to, retroviral envelopes, such as amphotrophic MLV envelope, for example. In addition, 293T cells are exemplified in the present invention, but many other cell lines also may be used. These include, but are not limited to, HeLa cells, COS cells, various T4 cell lines, HOS cells and D17 cells.

The generation of stable packaging cell lines, such as those provided in accordance with the present invention, increases the reproducibility and ease of creating high titer lentiviral stocks. The inducibility of the system eases biosafety concerns and the variation in expressed envelope proteins defines the tropism of the generated virus. Lentivirus systems permit the infection of non-dividing cells with high efficiency. The HIV-1 packaging cell line of the invention that produces authentic HIV-1 envelope protein is particularly useful for tissue specific screening of antiviral agents, and as a research tool to study the biology of HIV-1. Each of the vector cell lines of the invention can be used for human gene therapy protocols.

The following examples are provided to describe the invention in greater detail. They are intended to illustrate, not to limit, the invention.

EXAMPLE 1

Ecdysone-Inducible HIV-1 Packaging Cell Line Capable of Lineage-Specific Cell Transduction This example describes the creation of a stable, inducible lentiviral packaging cell line that generates titers ranging from $1.3$–$4.0 \times 10^5$ IU/ml. This titer can be further increased up to 16-fold by precipitating the viral supernatant using the calcium phosphate method prior to target cell infection. Expression of all HIV-1 proteins is tightly regulated in the packaging cells, under control of an ecdysone-responsive promoter. In the presence of the transcriptional inducer, viral gene expression is switched on and monitored by assessing titer, reverse transcriptase activity and p24 and Env protein expression. Vector virus from the line has the potential to specifically transduce non-dividing CD4+ lymphocytes, monocytes/macrophages, and glial cells in vivo. In addition, it has utility for studying HIV-1 biology and screening drug compounds for anti-HIV effects.

Methods

Ecdysone-inducible cell lines were generated using the Ecdysone-Inducible Expression Kit, (Invitrogen Corp., Carlsbad Calif.) essentially in accordance with the manufacturer's instructions. The kit enables production of an inducible gene expression system for mammalian cells utilizing the ecdysone analog, ponasterone A. The kit includes ponasterone A, the expression plasmid pIND, which contains five modified ecdysone response elements (E/GREs) upstream of a minimal heat shock. promoter and multiple cloning site, and a second plasmid, pVgRXR, which encodes the receptor subunits. The ecdysone-inducible system is shown schematically in FIG. 1.

Figure 2:
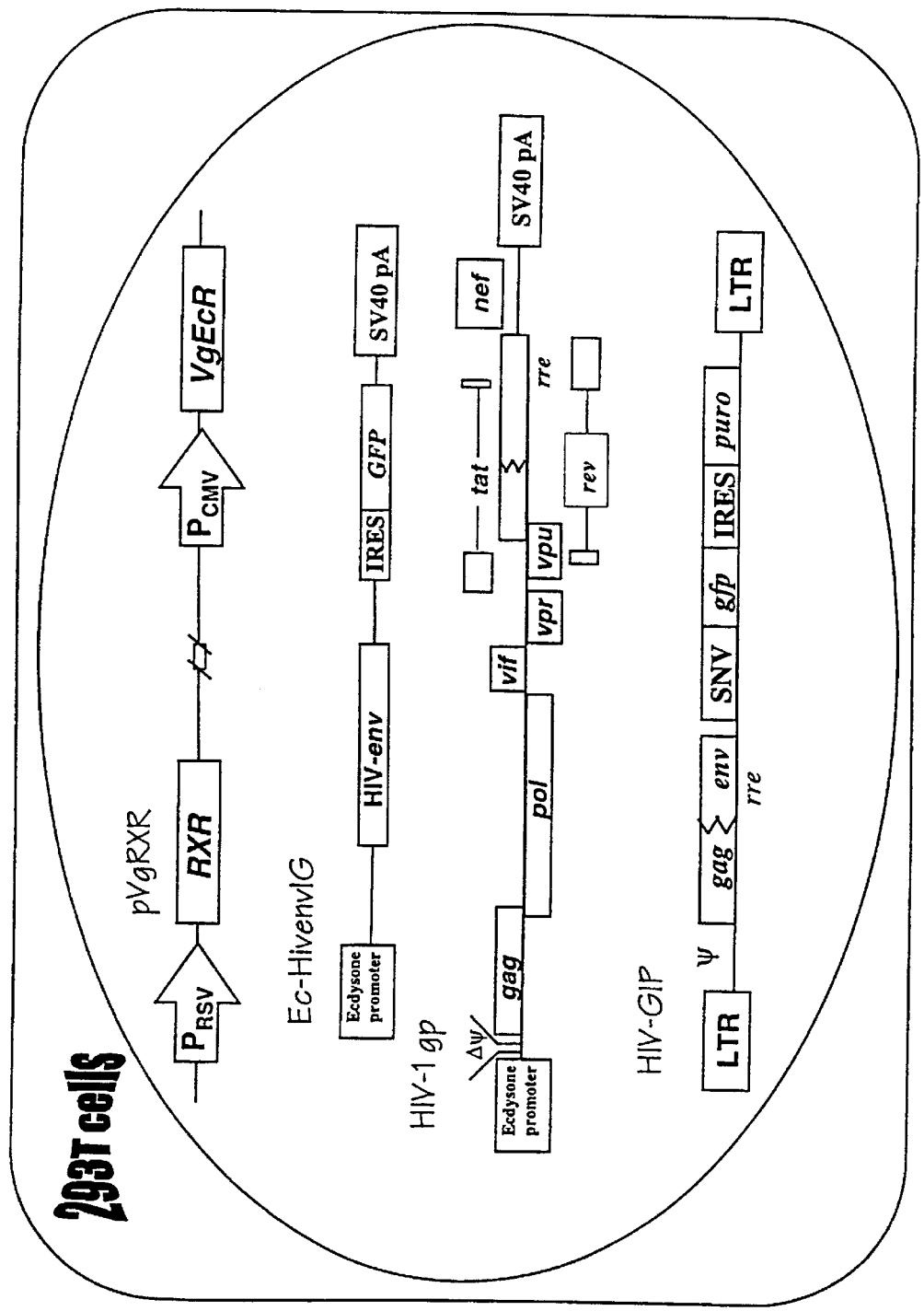
FIG. 2. Schematic diagram of the transfection of 293T cells with four DNA constructs, using the ecdysone inducible system. Encapsidation of the constructs expressing viral proteins is prevented by removal of all sequences before the 5' major splice donor (5'SD) including the 5' LTR, sequences between the 5'SD and the gag initiation codon, and part of the 3' LTR.

Two pIND plasmids were constructed, as shown diagramatically in FIG. 2. One pIND plasmid, referred to as EC-HivenviG, contained the HIV-1 gag gene and the GFP-encoding gene downstream of the ecdysone promoter element. The other pIND plasmid, referred to as HIV-1 gp, contained HIV-1 gag, pol, and HIV-1 accessory protein-encoding genes downstream of the ecdysone promoter element. A third construct (HIV-GIP), containing viral genes, a GFP-encoding gene and a puromycin resistance gene, was also made, as shown in FIG. 2.

The four constructs were transfected, along with pVgRXR, into 293T cells. After transfection, cells were treated with ponasterone A to induce intracellular expression from the two pIND-based constructs. The induction was accomplished by incubating the cells in 10 mM ponasterone A for 48 hours, then adding medium with ponasterone A in the absence of serum and incubating an additional 36 hours.

Viral vectors were concentrated by calcium phosphate precipitation. Following the 36 hour induction period, the culture supernatant was harvested and incubated for 1 hour at room temperature with 10 mM $CaCl_2$. The mixture was centrifuged 1 minute at $11,500 \times g$, and the pellet containing virus particles was resuspended in a minimum volume.

The concentrated virus preparation was used to infect HeLaT4 cells. Titers were scored by counting the number of green fluorescent target cells 2–3 days post infection. Titers were also confirmed by counting puromycin resistant colonies and by assessing reverse transcriptase activity in the infected cells.

Results

Transduction titers from four separate experiments are shown in the table below, comparing titers from stocks before and after calcium phosphate precipitation.

| | TITER (IU/ml) | | |
|---|---|---|---|
| | HeLaT4 | HeLa | |
| Target Cells Experiment # | Before Precipitation | After Precipitation | No Precipitation |
| 1 | $4.0 \times 10^5$ | ND (not done) | ND |
| 2 | $4.0 \times 10^5$ | ND | ND |
| 3 | $2.0 \times 10^5$ | $6.5 \times 10^6$ | ND |
| 4 | $1.3 \times 10^5$ | $1.6 \times 10^6$ | 0 |

Figure 3:
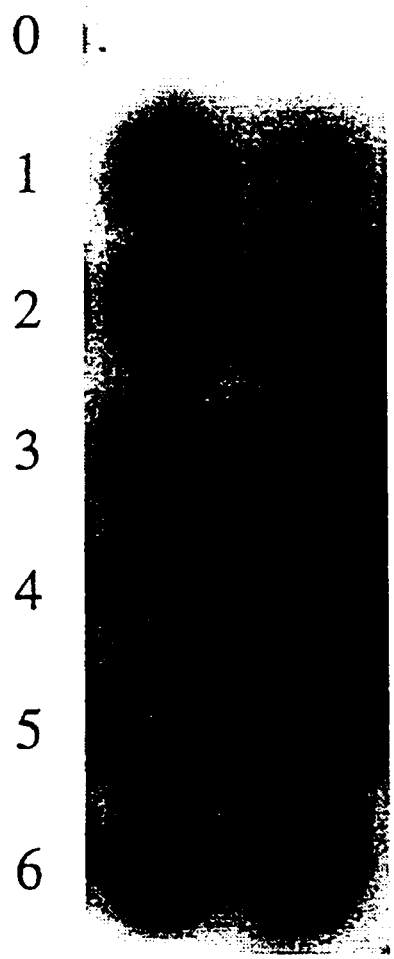
FIG. 3. Reverse transcriptase assay. Supernatant from the cell line was harvested on day 0 prior to induction, and on days 1 to 6 post induction, and analyzed for reverse transcriptase activity.
Figure 4:
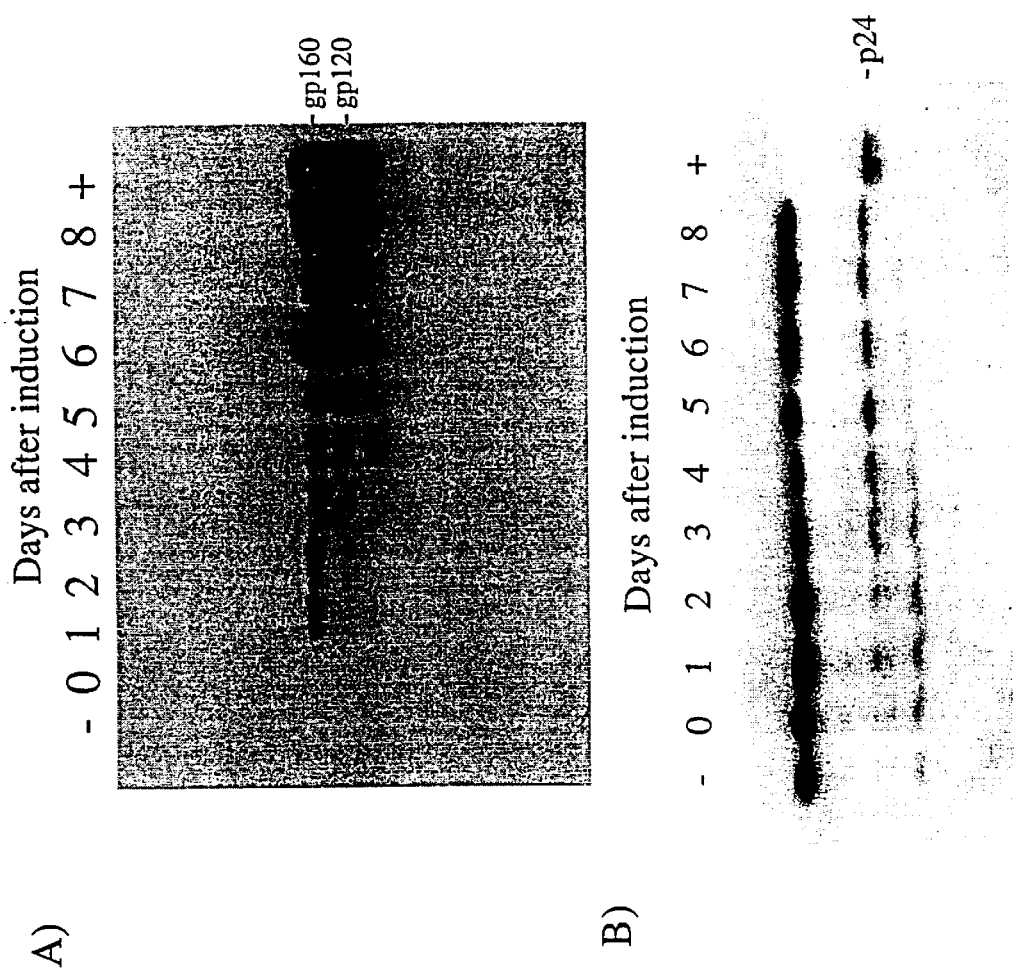
FIG. 4. Western blot analysis of inducible expression of (A) gp120 and (B) p24. Total cell protein from cell line was extracted on day 0 prior to induction and on days 1 through 8 post-induction, then probed with anti-p24 or anti-gp120 antibodies. + lane denotes cell lysate from HeLaT4 cells infected with wild type HIV-1 . − denotes cell lysates from uninfected HeLaT4 cells.

As can be seen, viral vector titers ranged from $1.3 \times 10^5$ to $6.5 \times 10^6$, depending on whether virus particles were concentrated by calcium phosphate precipitation. These titers were confirmed by counting puromycin resistant colonies. There was no virus detected before induction of the packaging line. Reverse transcriptase activity was also not observed in supernatant collected from the line before the addition of inducer, whereas it was detectable within 24 hours post induction (FIG. 3). Finally, western blotting to analyze inducible expression of gp120 or p24 further confirmed lack of expression of the transgenes prior to induction, and induction within 24–48 hours post-induction (FIG. 4).

EXAMPLE 2

Packaging Cell Line Deleted of All Non-Essential HIV-1 Proteins

This example describes the creation of a novel stable lentiviral packaging cell line devoid of tat, vif, vpr, vpu, and nef. Regulated expression from the packaging construct is achieved by placing the gag, pol, and rev genes under control of an inducible ecdysone promoter. Incorporation of the VSV-G envelope protein and the green fluorescent protein (GFP) into a second inducible plasmid allows us to simultaneously pseudotype the vector virus produced and observe the induction process while reducing the possibility of generating replication-competent virus. Moreover, because this cell line is stable and derived from individual clones, high-titer virus stocks can be generated reproducibly and repeatedly, effectively eliminating the need for subsequent transfections. The deletion of all nonessential HIV-1 proteins and the regulation of virion production from our system provides a novel and safe means for investigating its utility in in vivo gene therapy protocols.

Materials and Methods

Plasmid constructions. pVgRXR and the pIND expression vector are part of the Ecdysone-Inducible Expression Kit (Invitrogen K1001-01). pVgRXR encodes the heterodimeric ecdysone receptor subunits VgEcR and RXR. To construct pEcVIGhyg, the VSV-G envelope coding sequence was linked to the green fluorescent protein (GFP) by an internal ribosomal entry site (IRES) and was placed under transcriptional control of the inducible ecdysone promoter by cloning into pIND. Plasmid pEcgpr was constructed from pJJO1ΔBglII, a proviral clone of the LAI strain of HIV-1 which contains deletions in the encapsidation sequence from nucleotides 241–253 and 295–328 and a BglII deletion between nucleotides 6630 and 7215 which prevents expression of the env gene. An 8.3 kb BssHII-SacI fragment from JJOIΔBglII was ligated into the EcoRV site of pIND to generate pJS. pJS was digested with NdeI and XhoI which created a deletion between nucleotides 4710 and 9170. The 5.4 kb NdeI-XhoI pJS backbone was ligated to a 167 bp polymerase chain reaction (PCR) product containing the first exon of rev with its splice sites and a 1.9 kb NdeI-XhoI fragment containing the second exon of rev and the RRE. Thus, pEcgpr contains ecdysone-inducible open reading frames for Gag, Pol and Rev but has mutations, deletions or disruptions in the packaging signal (ψ), primer binding site (pbs), tat, vif vpr, vpu, env and nef. To construct the HIV-1 based retrovirus vector pCHSGIP, a 630 bp CMV promoter was precisely fused to the R-U5-pbs region of the 5' LTR of pHIV-GIP by PCR and cloned into pGEM-T Easy (Promega A1360). An XbaI-HaeII fragment containing the CMV-LTR fusion was ligated to 1.9 kb HaeII-BamHI and 5.9 kb BamHI-SpeI fragments from pEUV-GIP to yield pCHSGIP.

Packaging Cell Line Generation. 293T (human embryonic kidney) cells, HeLaT4 cells and HeLa cells were maintained in a 5% $CO_2$ atmosphere at 37° C. in Minimal Essential Medium (MEM) containing Earle's salts and L-glutamine (Gibco BRL 11095-080) and supplemented with 10% fetal bovine serum (Hyclone), 10×MEM non-essential amino acids (Gibco BRL 11140-050), 250 units/ml penicillin, and 250 μg/ml streptomycin (Gibco BRL 15070-063). All transfections were via the modified calcium phosphate precipitation method. To generate a stable cell line REr that conditionally expresses the heterodimeric ecdysone receptor subunits and gag, pol and rev, 293T cells were cotransfected with 10 μg pEcgpr and 25 ng pVgRXR which harbors the Zeocin resistance gene. Transfected cells were selected for resistance to 50 μg/ml Zeocin (Invitrogen R250-01) and individual colonies were screened for reverse transcriptase (RT) activity according to standard protocol before and after induction with 10 μM ponasterone A (Invitrogen H101-01). REr clones that exhibited the highest level of inducible RT activity were then transfected with 10 μg pEcVIGhyg and selected for hygr mycin resistance (150 μg/ml) (Calbiochem). Hygromycin resistant clones were split into two dishes in order to concomitantly maintain and test each clone for ponasterone A responsiveness. A high level of GFP expression in the presence of ponasterone A as determined by fluorescence microscopy (Zeiss Axiovert S100 inverted microscope) delineated the clone REr1.35 which represents the packaging cell line for the HIV-1 vector, pCHSGIP. The lentiviral producer cell line REr1.35.30 was established by transfection of 10 μg of the transfer vector pCHSGIP into REr1.35, selection with 1 μg/ml puromycin (Sigma) and evaluation of viral titer as described below.

Virus Production, Titer and Concentration. To test the viral titer, $3\times10^6$ REr1.35.30 cells were plated in 100 mm tissue culture dishes (Falcon 3003) in 10% MEM. Forty-eight hours later, the media were changed to 10% MEM containing 10 μM ponasterone A. On day 2 post-induction, the cells were re-fed with 10% MEM+10 μM ponasterone A. Supernatant was harvested on day 4 post-induction and viral titers were determined on HeLa cells as follows. Twenty-four hours before infection, HeLa cells were plated at a density of $3\times10^5$/60 mm tissue culture dish (Falcon 3002) in 10% MEM. On the day of infection, viral supernatant was collected and filtered through a 0.45 μm pore-size filter. Serial dilutions of the conditioned media were made in 10% MEM and added to the HeLa cells in the presence of 50 μg/ml polybrene (Sigma). The infections were gently rocked at 20 min intervals during their incubation at 37° C. After 2 h, the virus/polybrene solution was aspirated and the cells were refed with 10% MEM. Transduced cells were selected for puromycin resistance (1 μg/ml) 24 h after the infection. The puromycin resistant titer was corroborated by counting the number of GFP positive target cells using fluorescence microscopy.

To produce concentrated viral stocks, $6\times10^6$ REr1.35.30 cells were plated in 150 mm tissue culture dishes (Falcon 3025) in 10% MEM. Forty-eight hours later, the media were changed to 10% MEM containing 10 μM ponasterone A. Two days post-induction, the media were replaced with fresh 10% MEM+10 μM ponasterone A. Conditioned media were collected on day 4 post-induction, passed through a 0.45 μm pore-size filter, and ultracentrifuged at 4° C. in a Beckman 45Ti rotor at 50,000×g for 1.5 h. The viral pellet was resuspended in 10% MEM and subjected to a second ultra-centrifugation at 4° C. in the Beckman 45Ti rotor at 50,000×g for 1.5 h. The resulting viral pellet was resuspended in 10% MEM. Fresh concentrated viral supernatant was used to transduce either dividing or non-dividing HeLa cells at a multiplicity of infection (MOI) according to the method described below. Unused supernatant was stored at −70° C.

HIV-1 $p_{24}{}^{gag}$ Enzyme Linked Immunosorbent Assay (ELISA). The levels of p24 protein in samples of unconditioned (uninduced) or conditioned (days 1 through 4 post-induction) media from REr1.35 cells were determined by ELISA using a p24 ELISA kit according to the manufacturer's protocol (NEN Life Science Products).

Reverse Transcriptase Assay. Supernatant was collected from REr1.35 cells prior to induction and on days 1 through 4 after the addition of ponasterone A. RT activity was detected using a standard assay.

Immunoblotting. Uninduced and induced REr1.35 cells were. removed from 100 mm plates by treatment with trypsin, pelleted, washed three times with phosphate buffered saline (PBS) and resuspended in lysis buffer (50 mM Tris-HCl [pH 7.5], 150 mM NaCl, 5 mM EDTA, 1% NP-40, 10% glycerol) containing a protease inhibitor cocktail (Sigma P8340). Total cellular protein was quantified by using the BCA Protein Assay (Pierce). Thirty micrograms of total cellular protein were denatured by boiling for 5 min in loading buffer containing 0.2 M DTT. The proteins were separated by 10% SDS-PAGE and blotted onto polyvinylidene difluoride membrane (PVDF)(NEN Life Science Products). After blocking with 5% nonfat milk in TBS-T (150 mM NaCl, 50 mM Tris [pH 7.4], 0.1% Tween-20) for 1 h, the blots were incubated with mouse monoclonal anti-VSV-G (Sigma V5507) for 1 h at room temperature. The blots were washed with TBS-T and then incubated with sheep anti-mouse immunoglobulin conjugated to horseradish peroxidase (Jackson ImmunoResearch Laboratories) for 1 h at room temperature. After washing, protein bands were detected using the Renaissance chemiluminescence reagent as described by the manufacturer (NEN Life Science Products).

High MOI Transduction of Dividing and Non-Dividing Cells. One day prior to infection, dividing HeLa cells were plated in 10% MEM in a 24-well plate at a density of $10^4$ cells/well. Non-dividing cells were generated one day prior to infection by trypsinizing and resuspending HeLa cells in 1 ml of 10% MEM in a 15 ml tube (Falcon 2059). After exposure to 4000 rads of γ-irradiation, the cells were pelleted, diluted with fresh 10% MEM and plated at a density of $5\times10^4$ cells/well of a 24-well plate. The following day, $10^5$ virions were used to inoculate the dividing (MOI= 10) and irradiated HeLa cells (MOI=2) in the presence of 50 µg/ml polybrene at 37° C. for 2 h. After the incubation, the virus/polybrene solution was aspirated and replaced with 10% MEM. In the absence of puromycin selection, fluorescence microscopy was used to assess GFP gene delivery to the dividing and non-dividing HeLa cells.

Assays for Replication-Competent Virus.

(i) Marker rescue assay. To generate the marker rescue cell line MRC-CH,HeLaT4 cells were transduced with vector virus produced from RErl.35.30 and placed on puromycin selection to ensure that each cell harbored at least one copy of the CHSGIP provirus. The marker rescue assay was carried out as follows: Using the protocol described for virus titration given above, MRC-CH cells were transduced with concentrated vector stock and passaged for 4 weeks in the absence of antibiotic selection. After such time, conditioned supernatants were filtered through a 0.45 µm pore-size filter and used undiluted to infect virgin HeLa cells using the same protocol. The transduced HeLa cells were maintained in the absence of selection and were subsequently scored for GFP expression using fluorescence microscopy. To demonstrate that the integrated provirus was capable of being rescued, supernatant containing wild-type HIV-$1_{LAI}$ was used to infect MRC-CH cells according to the protocol described above. After 3 weeks of passage in the absence of antibiotic selection, conditioned supernatant from the transduced MRC-CH cells was harvested, passed through a 0.45 µm pore-size filter and used to infect fresh HeLaT4 cells. Fluorescence microscopic examination of the transduced HeLaT4 cells revealed numerous GFP$^{++}$ cells. This positive control ensured that the provirus could be rescued and, therefore, replication-competent virus would be detected with this system. Vector stocks are considered replication-incompetent when no GFP$^+$ cells are detected.

(ii) HIV gag transfer assay. Supernatant samples from MRC-CH cells inoculated with virus stock were harvested after 2 weeks and 4 weeks of passage in culture. The concentration of p24$^{gag}$ in these supernatants was measured by ELISA using a p24 ELISA kit according to the manufacturer's protocol (NEN Life Science Products). Virus preparations are considered helper free when the p24 concentration falls below the detection threshold which, for this assay, was determined to be $\geq1.2$ pg/ml.

(iii) Reverse Transcriptase Assay. HeLa cells previously incubated with supernatant from transduced MRC-CH cells were passaged 4 weeks in culture and the supernatant was tested for the presence of RT using the standard procedure.

Flow Cytometric Analysis. Transduced HeLa cells were trypsinized, washed twice with PBS and resuspended in 0.3 ml PBS. Flow cytometry was performed using an EPICS Profile II (Coulter Corporation) outfitted with the Elite program (version 4.01; Coulter Corporation).

Results

Strategy for Generation of Inducible Lentiviral Packaging Cell Line. Packaging cells based on HIV-1 have been difficult to develop in large part due to the cytotoxicity associated with constitutive high-level expression of the VSV-G envelope protein used for pseudotyping the virus to be produced. In addition, regulated HIV-1 protease production would be beneficial since it has been reported to have cytopathic effects and would provide an additional level of safety. Employing an inducible system allows for regulated expression of cytotoxic proteins since their transcription only occurs upon addition of the corresponding inducer. The tetracycline-regulated system is a widely used and well characterized example of an inducible system. However, it has been reported that high level expression of the transactivating fusion protein tTA can be cytotoxic. We therefore selected an ecdysone inducible expression system to provide regulated production of all trans-acting proteins. The system is based on the ability of an ecdysone analog, ponasterone A, to activate transcription through a heterodimer which has been modified to allow gene expression in mammalian cells. The heterodimer consists of an ecdysone receptor (VgEcR) which contains the VP16 transactivation domain from Herpes simplex virus and its binding partner, the retinoid X receptor (RXR). Addition of ponasterone A causes the VgEcR/RXR heterodimer to bind to a hybrid ecdysone response element and to activate gene transcription from a minimal heat shock promoter through the action of the VP16 domain contained in VgEcR.

Figure 5:
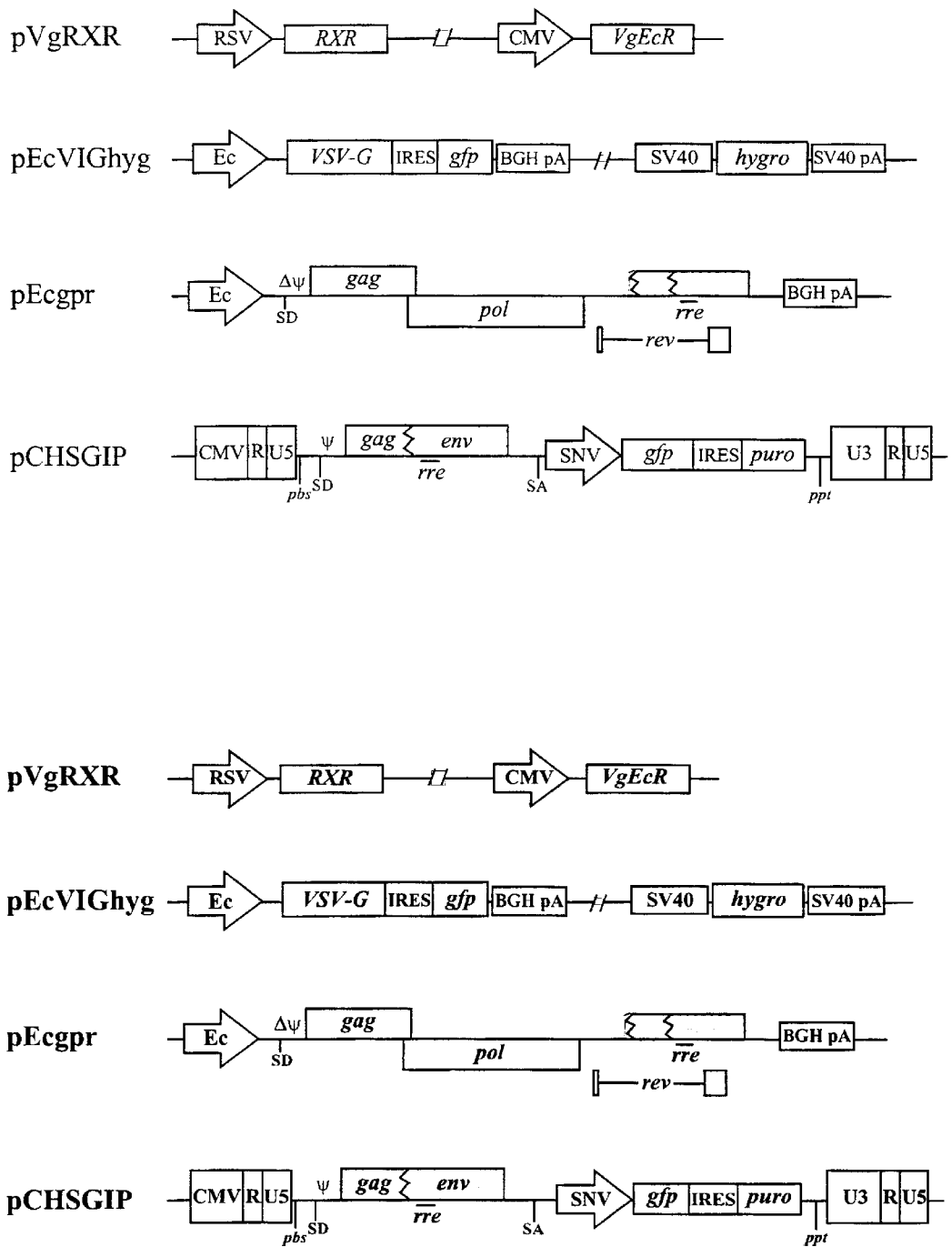
FIG. 5. Schematic diagrams of the expression plasmids and retroviral vector used to establish the stable, inducible lentiviral vector producer cell line described in Example 2. pVgRXR encodes the subunits of the transcriptional heterodimer. Boxes shaded with diagonal lines depict nonfunctional HIV-1 genes. The construction of pEgpr, pEcVIGhyg and pCHSGIP are described in detail in the example. Abbreviations and symbols: $\Delta\psi$ represents a 33-bp deletion within the encapsidation signal downstream of the splice donor site. RSV, Rous sarcoma virus promoter; CMV, immediate-early promoter from human cytomegalovirus; Ec, inducible ecdysone promoter; VSV-G, coding sequence for the G envelope protein from vesicular stomatitis virus; IRES, internal ribosomal entry site from encephalomyocarditis virus (EMCV); gfp, sequence encoding the green fluorescent protein; BGH pA, bovine growth hormone polyadenylation signal; SV40, SV40 early gene promoter; hygro, hygromycin gene; SV40 pA, SV40 polyadelylation signal; SNV, spleen necrosis virus U3 promoter; puro, puromycin gene.

Construction of the Packaging Cell Line. To begin, we generated a ponasterone A-responsive 293T-based cell line which produces HIV-1 structural and enzymatic, proteins by cotransfecting the pVgRXR plasmid which contains coding sequences for both the VgEcR/RXR heterodimer and zeocin resistance, along with a packaging plasmid, pEcgpr (FIG. 5). This packaging construct contains sequences necessary for transcription of gag, pol, and rev by the upstream ecdysone promoter and has deletions of tat, vif, vpr, vpu, and nef (FIG. 5). Sixty-eight stably transfected zeocin resistant clones were screened for the presence of the packaging plasmid by assaying for RT activity in the absence and presence of ponasterone A as described in Materials and Methods. We chose the cell line with the highest level of induction and RT enzymatic activity, designated RErl, for further development.

The envelope construct pEcVIGhyg used in the creation of the inducible packaging cell line contains coding sequences for the VSV-G envelope protein and GFP under transcriptional control of the inducible ecdysone promoter as well as a gene which confers hygromycin resistance to transfected cells (FIG. 5). An internal ribosomal entry site (IRES) allows translation of GFP to occur in a cap-independent manner. RErl cells were transfected with pEcVIGhyg and selected for hygromycin resistance. Thirty-eight hygromycin resistant, nonfluorescing cell clones were induced with ponasterone A and screened by fluorescence microscopy for induction of GFP expression. Cell clones exhibiting the highest level of induction and the most homogenous GFP positive population were chosen as putative packaging cell lines. Because the production of reverse transcriptase and GFP does not provide direct evidence of an individual cell clone's ability to package and produce virus, and since the transient titer of a particular clone is one indication of its ability to produce functional viral proteins, we chose to evaluate the potential of each of the clones to package and produce viable virus particles. The abovementioned cell clones were transiently transfected with the transfer vector pCHSGIP, induced with ponasterone A and titered on HeLa cells according to the protocol described in Materials and Methods. The clone we designate as REr1.35 had the highest transient titer among all the clones that were screened. Accordingly, we chose to characterize this particular stable, inducible packaging cell line and evaluate its potential to become a stable, high-titer lentiviral vector producer cell line.

Figure 6A:
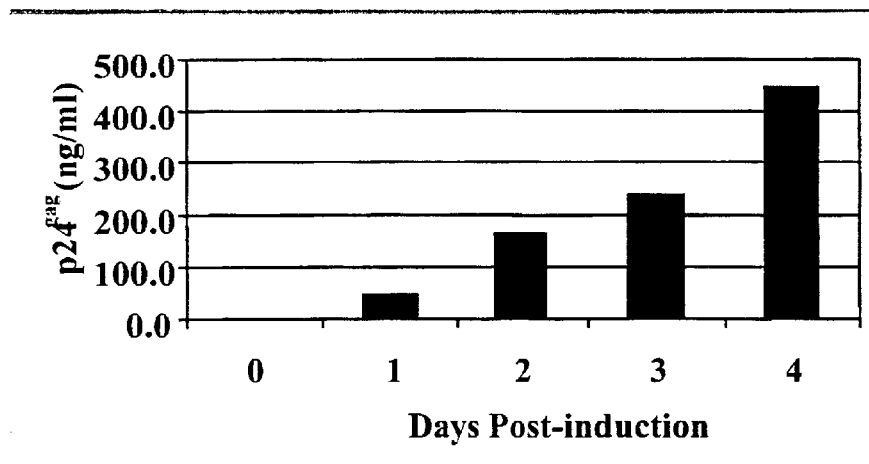
(FIG. 6A) Induction of $p24^{gag}$ expression. Supernatant from REr1.35 packaging cells was collected on Day 0 prior to induction with ponasterone A and on days 1 through 4 post-induction. The amount of $p24^{gag}$ in each sample was determined using a commercial ELISA kit.
Figure 6B:
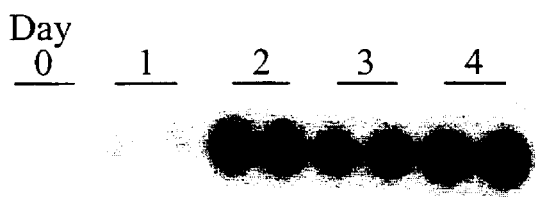
(FIG. 6B) Upregulation of RT expression. Supernatant samples from REr1.35 packaging cells were taken prior to induction and on days 1 through 4 post-induction followed by measurement of RT activity as described in Materials and Methods.
Figure 6C:
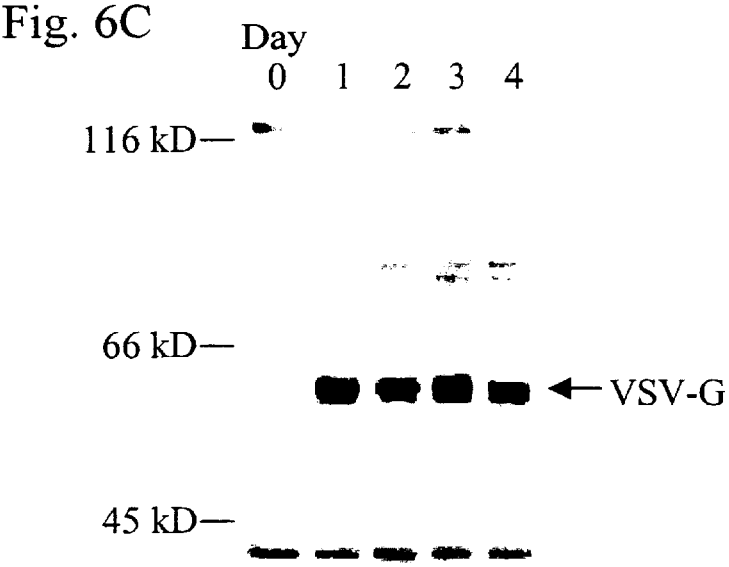
(FIG. 6C) Western blot analysis of inducible VSV-G expression. Cell lysates were harvested from uninduced (Day 0) and induced (Day 1 through 4) REr1.35 cells and total protein was electrophoresed through a 10% SDS-polyacrylamide gel. After transfer, the membrane was probed with a mouse monoclonal antibody specific for VSV-G as outlined in Example 2. The position of the VSV-G protein is indicated by the arrow.

The time course of inducible expression of viral proteins from the REr1.35 packaging cell line was investigated using three different approaches whose results are displayed in FIG. 6. First, production of the HIV-1 gag protein product p24 in conditioned media was determined by ELISA. The concentration of $p24^{gag}$ was found to be below the threshold of detection prior to addition of ponasterone A and reached maximal amounts four days post-induction (FIG. 6A). Then, HIV-1 RT, a product of the pol gene, was measured by assaying for its enzymatic activity in the supernatant taken from REr1.35 cells before and during induction with ponasterone A (FIG. 6B). RT activity was undetectable prior to induction and was clearly present in increasing amounts on days 1 through 4 post-induction. Additionally, we examined cell lysates prepared from REr1.35 for the presence of the VSV-G envelope protein before induction with ponasterone A and on days 1 through 4 after induction. A Western blot demonstrating the inducible expression pattern of the VSV-G envelope protein is displayed in FIG. 6C. A high level of expression of VSV-G only occurred after addition of the inducer and persisted for at least 4 days. The complete absence of viral protein production before induction with ponasterone A paired with the rapid onset and abundant yield subsequent to induction demonstrate the tight regulation and high level of protein expression that can be achieved using the ecdysone inducible system.

Production of Lentiviral Vectors from REr1.35. Most of the previously reported packaging cell systems depend on the transcriptional transactivator Tat in order to achieve high-level transcription of the viral genome and transgene from the HIV-1 LTR. However, it has been shown that Tat is dispensable for virus production provided there is a high enough level of transcription of the viral genome from a constitutive promoter and any genes of interest are expressed from a heterologous promoter. Taking this into consideration, we created a Tat-independent transfer vector for inclusion in our accessory null system. The U3 in the 5' LTR of the transfer vector pCHSGIP (FIG. 5) was replaced with the constitutive immediate-early enhancer/promoter of human cytomegalovirus (CMV) while GFP and the puromycin resistance gene are expressed from a separate SNV-U3 promoter within the body of the vector.

To generate the stable producer cell line, the pCHSGIP plasmid was transfected into REr1.35 cells and twenty-five GFP positive, puromycin resistant clones were isolated. Constitutive expression of GFP from pCHSGIP facilitated selection of stable cell clones since the REr1.35 cells were uninduced at the time of transfection and hence, the GFP harbored by the pEcVIGhyg plasmid was not being transcribed. Each of the isolated cell clones was examined for their capacity to produce high-titer virus by culturing in media containing 10 µM ponasterone A. After 48 h, the culture media were replaced with fresh media containing a second dose of 10 µM ponasterone A. Forty-eight hours after the second addition of ponasterone A, conditioned media were harvested and used to infect target cells. Based on its preliminary titer of $0.4 \times 10^5$, the cell clone REr1.35.30 was chosen as the stable, inducible lentiviral vector producer cell line.

In order to obtain the highest titer virus possible, we decided to further characterize the producer cell line by determining the optimal time for viral harvest after induction. Conditioned supernatant from REr1.35.30 was collected before and at successive time points after induction with ponasterone A (Table 1).

TABLE 1

Transduction Titers from REr1.35.30[a]

| Day[b] | Titer (IU/ml) |
| --- | --- |
| 0 | 0 |
|   | 0 |
| 1 | $1.8 \pm 2.6 \times 10^2$ |
|   | $4.1 \pm 3.1 \times 10^3$ |
| 2 | $1.8 \pm 0.2 \times 10^4$ |
|   | $3.1 \pm 0.5 \times 10^4$ |
| 3 | $4.0 \pm 0.4 \times 10^4$ |
|   | $1.0 \pm 2.5 \times 10^5$ |
| 4 | $1.0 \pm 1.4 \times 10^5$ |
|   | $1.0 \pm 0.3 \times 10^5$ |
| 5 | $1.8 \pm 0.2 \times 10^5$ |
|   | $6.7 \pm 2.2 \times 10^4$ |

Maximal titers observed 4 days post-induction ranged from $0.8 \times 10^5$ to $1.2 \times 10^5$ IU/ml. Virus produced from this cell line is pseudotyped with the VSV-G envelope protein, making it amenable to concentration by ultracentrifugation. We examined this potential for concentration by collecting and pooling conditioned supernatant from REr1.35.30 four days after induction and subjecting it to two consecutive rounds of ultracentrifugation as outlined in the Materials and Methods. With recoveries averaging 74%, the pseudotyped virus produced from REr1.35.50 could be concentrated up to 1400-fold to achieve titers upwards of $0.8 \times 10^8$ IU/ml (Table 2).

TABLE 2

Transduction Titers With REr1.35.30 Day 4 Conditioned Media.[a]

|  | Titer (IU/ml) | |
| --- | --- | --- |
| Experiment | Unconcentrated[b] | Concentrated[b] |
| 1 | $0.9 \pm 2.0 \times 10^5$ | $0.2 \pm 0.4 \times 10^8$ |
| 2 | $0.8 \pm 1.2 \times 10^5$ | $0.6 \pm 0.3 \times 10^8$ |
| 3 | $0.4 \pm 1.7 \times 10^5$ | $0.2 \pm 0.5 \times 10^8$ |
| 4 | $0.3 \pm 2.3 \times 10^5$ | $0.2 \pm 0.7 \times 10^8$ |
| 5 | $0.6 \pm 1.6 \times 10^5$ | $0.8 \pm 0.9 \times 10^8$ |

Even though the possibility of generating wild type HIV-1 is virtually non-existent in our system because the majority of the HIV-1 genes have been deleted, the production of any type of replication-competent virus would be a liability. Therefore, viral stocks propagated from REr1.35.30 were tested for the presence of replication-competent virus by employing three independent methods: (i) a marker rescue assay which utilizes MRC-CH, a HeLaT4-based cell line which harbors the CHSGIP provirus (FIG. 5); (ii) the detection of HIV gag transfer to vector-transduced MRC-CH cells by $p24^{gag}$ ELISA; and (iii) a reverse transcriptase assay on supernatant collected from vector-transduced MRC-CH cells. The results obtained from all three procedures indicated that conditioned media produced from the REr1.35.30 cell line were always free of replication-competent virus.

Characterization of Recombinant Virus Produced from REr1.35.30. That lentiviral vectors have the ability to traverse the nuclear envelope barrier regardless of the mitotic state of the target cell is integral for their use in in vivo gene delivery. The efficiency with which vectorvirus produced from REr1.35.30 could transduce non-dividing cells was examined in parallel with a Gibbon ape leukemia virus (GALV)-pseudotyped MLV-based vector and a VSV-G pseudotyped HIV-1-based vector containing accessory proteins. All of the viral vectors harbor the gene for expression of GFP which facilitated scoring infected target cells in the absence of puromycin selection. HeLa cells which were growth arrested at the $G_2$ stage of the cell cycle by γ-irradiation were inoculated with the HV-1-based or MLV-based vectors at comparable multiplicities of infection (MOI). Virus produced from REr1.35.30 was able to efficiently infect the non-dividing cells in proportions similar to its VSV-G pseudotyped HIV-1-based vector counterpart which harbors accessory proteins. In contrast, the MLV-based vector virus was incapable of gene transfer to the irradiated targets. This experiment verifies that the absence of accessory proteins from our packaging cell line does not affect the ability of the virus produced to efficiently infect growth arrested target cells.

While gene delivery to cells with a low mitotic index is an important consideration when establishing a lentiviral vector producer cell line, it is equally important to achieve a high efficiency of gene transfer. This goal can be accomplished by concentrating VSV-G pseudotyped lentiviral vectors to yield high-titer virus stocks capable of transducing a maximal number of target cells. However, caution must be exercised when estimating transduction efficiencies since it has been reported that concentrated VSV-G pseudotyped retroviral vectors may lead to an artificially elevated efficiency of gene transfer brought, about by passive protein transfer, or pseudotransduction. To demonstrate efficient gene transfer and ensure the absence of pseudotransduction by GFP, we infected HeLa cells with virus concentrated from REr1.35.30 (MOI=10) and maintained them in the absence of puromycin selective media. Two days and fourteen days after infection, the targeted HeLa cells were harvested and subjected to flow cytometric analysis in order to accurately determine the percentage of GFP+ target cells. We found that the proportion of GFP+ HeLa cells averaged 28.8% forty-eight hours post-infection and 36.5% two weeks post-infection with GFP expression persisting for a minimum of 5 weeks. Passive protein transfer should result in a precipitous decrease in the proportion of GFP+ target cells because the protein transferred should not persist in any of their daughter cells. Based on our observations, we concluded that virus produced from REr1.35.30 can achieve efficient gene delivery and long term expression in the absence of pseudotransduction.

The present invention is not limited to the embodiments described and exemplified above, but is capable of variation and modification without departure from the scope of the appended claims.

We claim:

1. A transgenic mammalian packaging cell line generated from cultured cells selected from the group consisting of 293T cells and HeLa cells for producing HIV-1 lentiviral vectors, the cell line comprising:
   a) a DNA construct expressing a transcription factor responsive to ecdysone, muristerone A, or ponasterone A; and
   b) one or more DNA constructs comprising
      i) one or more HIV-1 genes required for packaging of a lentiviral vector; and
      ii) an HIV-1 env gene encoding a HIV-1 viral envelope protein; wherein the lentivirus genes and the gene encoding a viral envelope protein are operably linked to at least one DNA response element acted upon by the transcription factor, the cell line being transfectable with the lentiviral vector, and wherein the HIV-1 genes and the HIV-1 env gene are introduced into the cell line on separate vectors.

2. The cell line of claim 1, comprising HIV-1 core genes, regulatory genes and accessory genes.

3. A method for producing a HIV-1 lentivirus vector stock, comprising the steps of:
   a) providing a mammalian packaging cell line generated from cultured cells selected from the group consisting of 293T cells and HeLa cells comprising:
      i) a DNA construct expressing a transcription factor responsive to muristerone A or ponasterone A; and
      ii) one or more DNA constructs comprising one or more HIV-1 genes required for packaging of a lentiviral vector, and a gene encoding HIV-1 a viral envelope protein; wherein the packaging genes and the gene encoding a HIV-1 envelope protein are operably linked to at least one DNA response element acted upon by the transcription factor, the cell line being transfectable with the lentiviral vector;
   b) transfecting the cell line with a lentivirus vector deficient in one or more genes requied fro packaging and in the env gene
   c) exposing the transfected cell line to muristerone A or ponasterone A for a time and under conditions enabling activation of the transcription factor and resultant induction of expression of the genes operably linked to the DNA response element, thereby producing proteins required for the packaging of the lentiviral an HIV-1 vector into virus particles, thereby producing the lentivirus HIV-1 vector stock.

4. The method of claim 3, wherein the virus stock is an HIV-1 vector virus stock with a titer of at least $1 \times 10^5$.

5. The method of claim 3, wherein the virus stock is an HIV-1 vector virus stock with a titer of at least $1 \times 10^7$.

* * * * *